United States Patent [19]
Sorensen

[11] 4,275,722
[45] Jun. 30, 1981

[54] RESPIRATORY EXERCISER AND REBREATHING DEVICE

[76] Inventor: Harry D. Sorensen, 740 Conrad Rd., Niles, Mich. 49120

[21] Appl. No.: 36,093

[22] Filed: May 4, 1979

[51] Int. Cl.³ .............................................. A61M 16/00
[52] U.S. Cl. ............................ 128/200.24; 128/203.12; 128/205.27; 128/914
[58] Field of Search ................... 128/205.11, 205.12, 128/205.17, 200.24, 204.18, 203.12, 203.25, 203.28, 203.29, 205.13, 205.25, 205.24, 205.27, 205.28, 205.29, 205.14; 272/99 R

[56] References Cited

U.S. PATENT DOCUMENTS

| | | | |
|---|---|---|---|
| 693,795 | 2/1902 | Giersberg | 128/205.12 |
| 2,007,330 | 7/1935 | Hicks | 128/203.28 |
| 3,455,294 | 7/1969 | Adler et al. | 128/201.18 X |
| 3,513,843 | 5/1970 | Exler | 128/203.25 |
| 4,086,923 | 5/1978 | Henkin | 128/205.11 |

*Primary Examiner*—Henry J. Recla
*Attorney, Agent, or Firm*—Marmaduke A. Hobbs

[57] ABSTRACT

A respiratory exerciser and rebreathing device in which inhalation and exhalation chambers are provided for mixing exhaled air with ambient air to increase the carbon dioxide content of the air to be inhaled. A mouthpiece and a valve device between the mouthpiece and the chambers for directing the air flow are provided, and an adjustable mechanism is used to vary the amount of exhaled air which is mixed with ambient air to be rebreathed. Condensation plates in the inhalation chamber remove moisture from the air which is inhaled. The breathing pressures required to operate the device may be variable, in order to control the exercise of the muscles of respiration.

16 Claims, 11 Drawing Figures

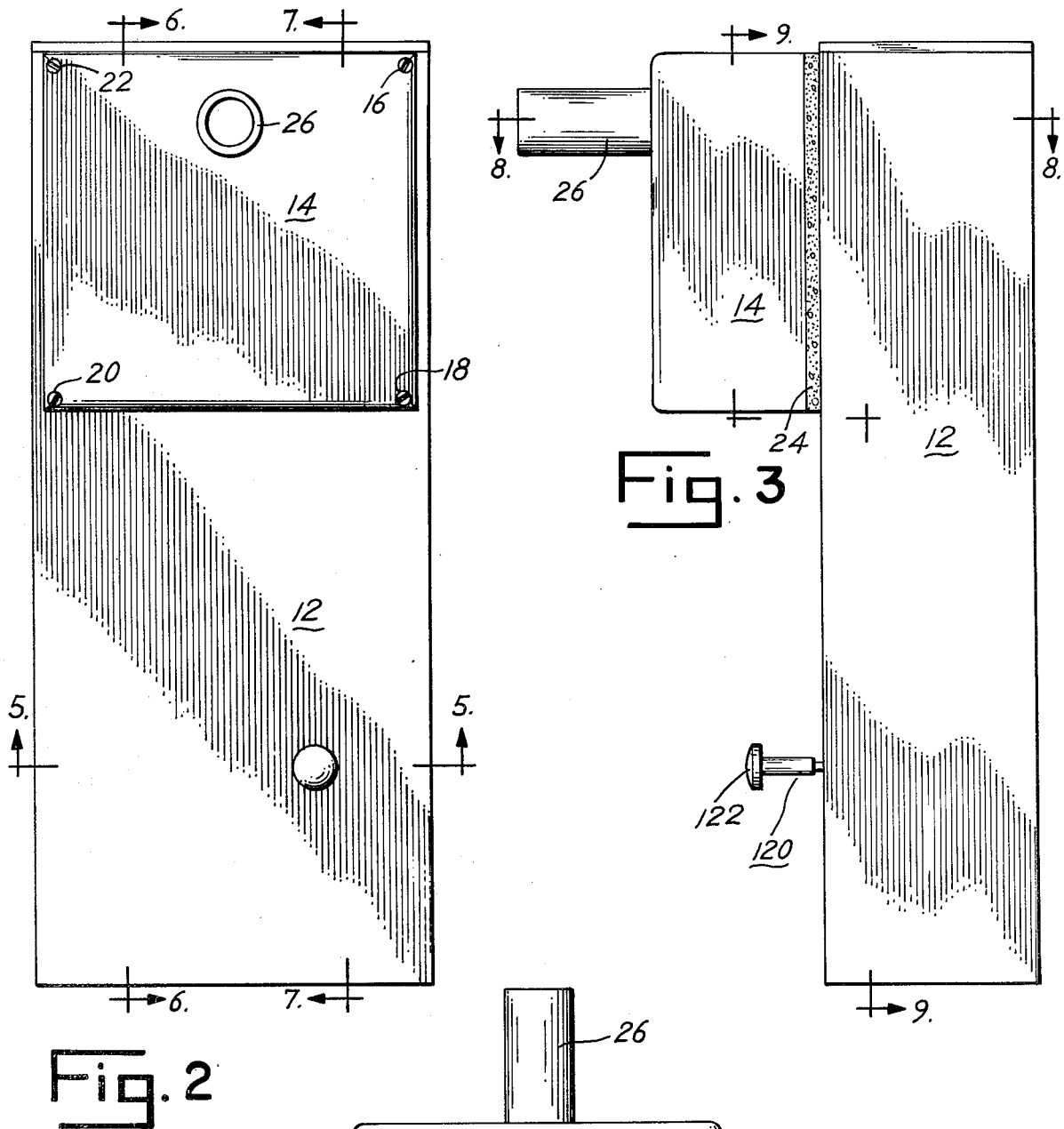

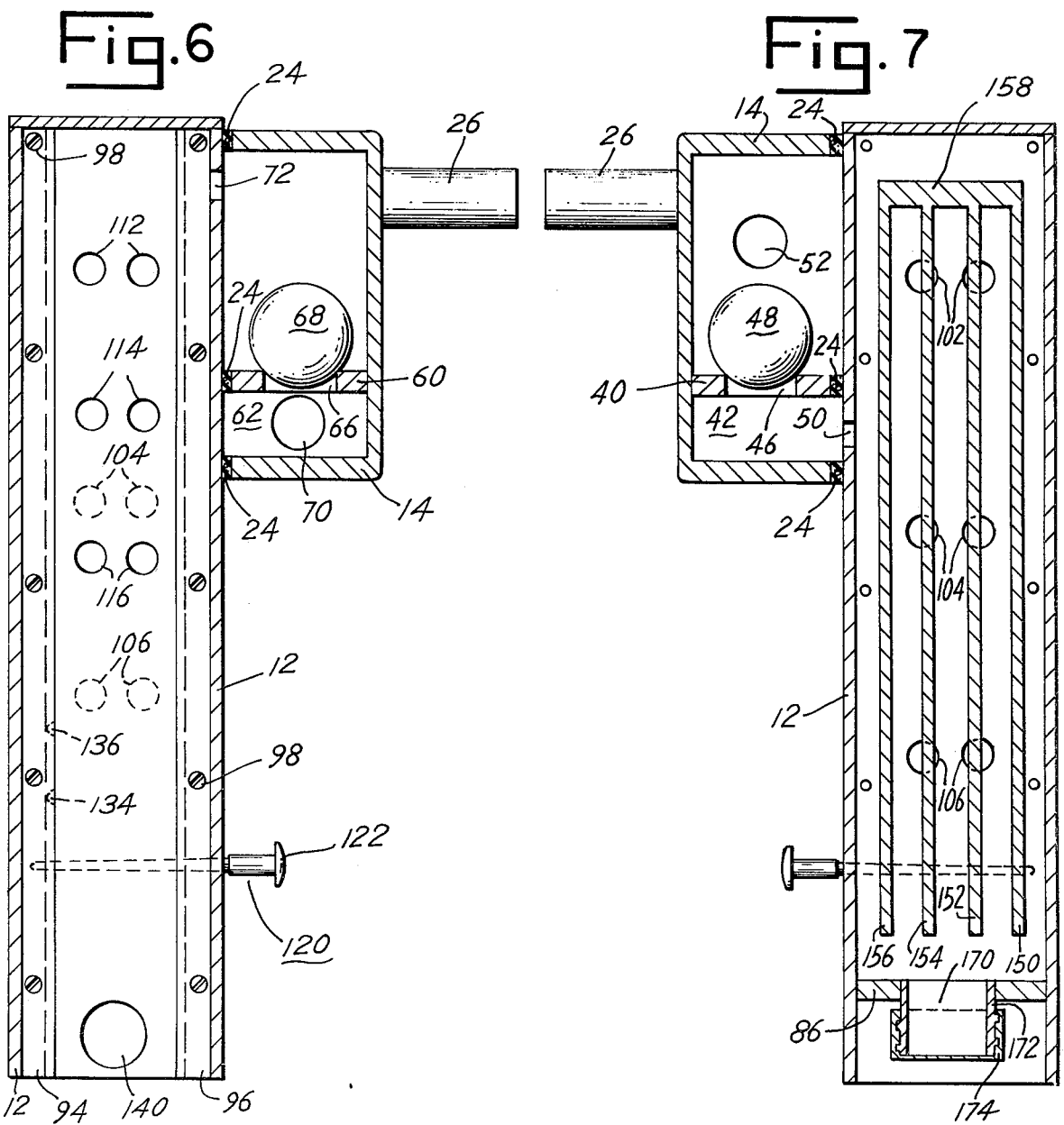

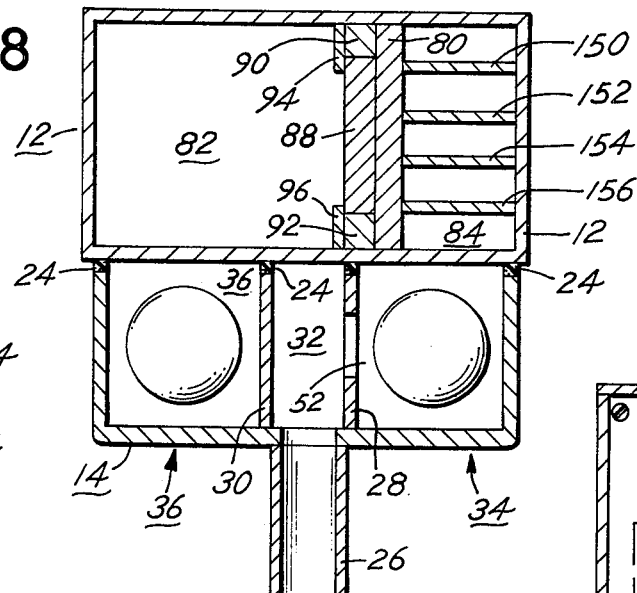
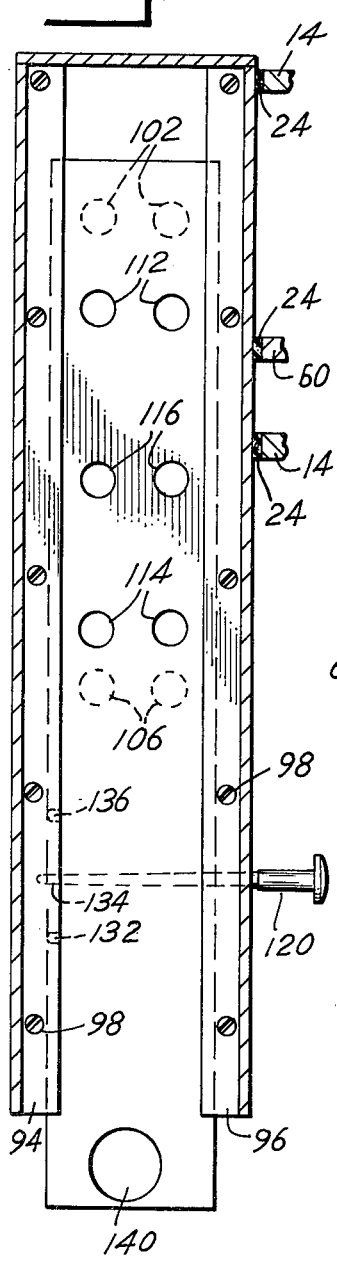
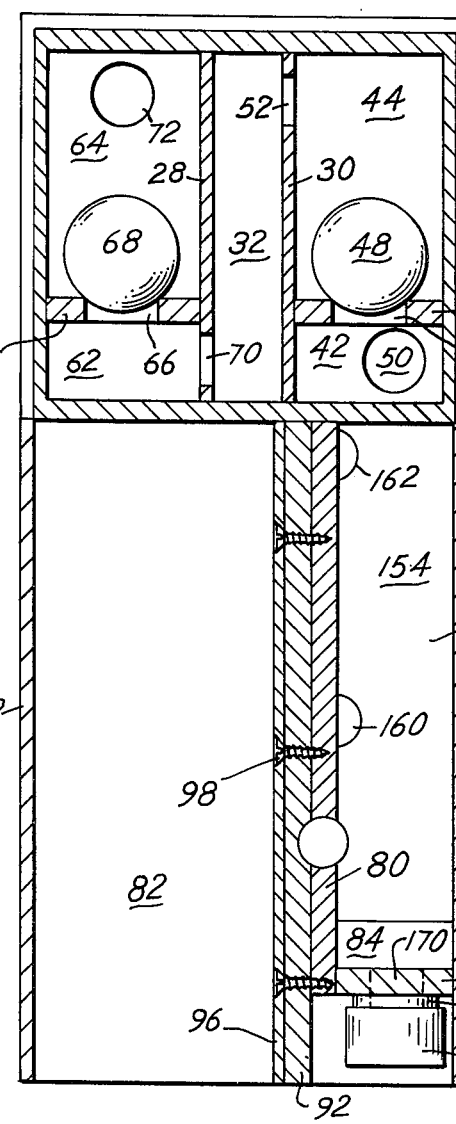
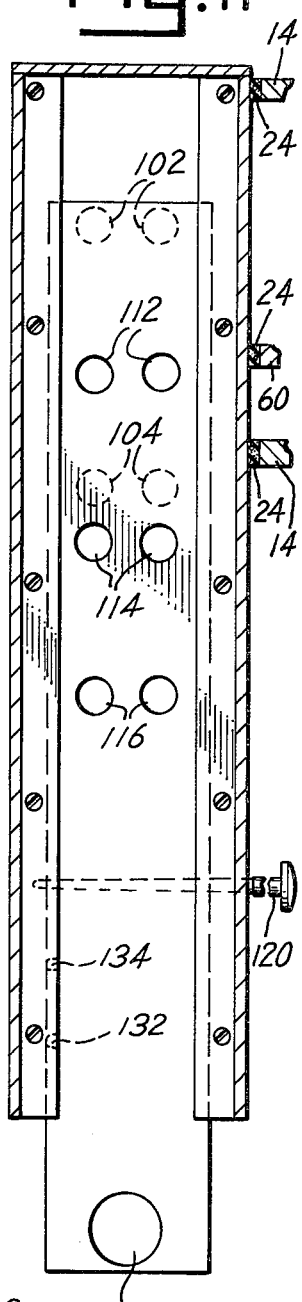

RESPIRATORY EXERCISER AND REBREATHING DEVICE

The basic function of the respiratory system is to supply oxygen to and to remove carbon dioxide from the blood stream. The mechanism involved in accomplishing this function is that during the inhalation phase of respiration, air is taken into the lungs where it finally comes to be held in small air sacs known as alveoli. Closely associated with the thin walls of the alveoli are small blood capillaries which allow gases to pass by means of diffusion, whereby gases in the area of higher concentration pass to the area of lower concentration to equalize the concentration between the two areas. Hence, since the air which is normally taken in during the inhalation phase of respiration is higher in concentration of oxygen and lower in concentration of carbon dioxide than is the blood stream, diffusion in the area of alveoli occurs such that oxygen passes from the alveoli into the blood in the capillaries and carbon dioxide from the blood passes to the alveoli from where it eventually leaves the body in the exhalation phase of respiration. Chemoreceptors of the aorta and carotid arteries detect various blood gas levels. When there is an increase in concentration of carbon dioxide in the blood or decrease in the oxygen concentration level, such as occurs during exercise when the muscles use greater amounts of oxygen and give off greater amounts of carbon dioxide, the change is detected by the chemoreceptors. Nerve impulses are then transmitted to the medulla which triggers respiration changes, the rate of respiration will quicken, and longer, deeper, breaths will be taken. Changes in the blood chemistry can also trigger increased heart rates and other physical changes in an attempt to compensate for the change in the blood gas levels and to establish normal levels. These reactions occur automatically when the changes are detected in the blood gas concentrations.

It has been discovered that exercise of these compensatory mechanisms will create increased efficiency in the respiration system. Physical exercise has long been used to accomplish this; however, this requires both time and room in which to exercise. It often requires considerable time to go to a gymnasium or swimming pool to perform exercises, and it may require special clothing as well as time to prepare for and to shower or otherwise clean up after such exercise. Thus, it can only be done when a substantial amount of time is available for performing the exercise, and if done outdoors, the exercise period is dependent upon weather conditions as well.

Various devices have been designed in an attempt to create chemical changes within the blood similar to those which occur during exercise. These devices have commonly been used for respiratory exercise by persons with physical incapacities which prevent them from engaging in physical exercise, and for surgical patients and the like who must perform respiratory exercise to prevent post surgical complications. The previous designs of respiratory exercise devices have many drawbacks; they are often designed to be a closed system so that prolonged use continually increases the carbon dioxide level and decreases the oxygen level of the system, never achieving a balanced level. They often are not adjustable, so that a predetermined carbon dioxide concentration level cannot be selected nor can the muscles of respiration be increasingly stressed. One of the greatest difficulties in using the previous devices is that prolonged use creates an excessively high moisture content in the rebreathed air. Exhaled air is significantly higher in moisture content that is fresh air, and continually rebreathing exhaled air continually increases the moisture content of the rebreathed air. Severe complications may arise from breathing air with exceptionally high moisture content, and the previous designs for respiratory exercise devices have not provided means for removal of moisture from the rebreathed air.

It is one of the principal objects of the present invention to provide an adjustable respiratory exerciser and rebreathing device which will provide increased carbon dioxide concentrations and decreased oxygen concentrations to the user, and which will thereby create increased carbon dioxide and decreased oxygen concentration levels in the blood stream, together with the resultant physical and bodily compensatory changes, and which is adjustable so as to provide various preselected gas concentration levels.

Yet another object of the present invention is to provide an adjustable respiratory exerciser and rebreathing device which will provide muscular exercise for the muscles of respiration, and will promote good breathing mechanics, and which is adjustable so as to provide varying levels of muscular exercise.

A further object of the present invention is to provide an adjustable respiratory exerciser and rebreathing device which provides the respiratory benefits normally obtained from physical exercise without the need to use a gym, swimming pool or the like, which can be used at any time, anywhere, in a sitting or standing position without the need of special clothing or great lengths of time, and which can be used any time of the year, indoors or out, regardless of the weather conditions.

A still further object of the present invention is to provide an adjustable respiratory exerciser and rebreathing device which can be used by the physically impaired or handicapped, the elderly or otherwise physically infirm, which is convenient to use, is hand held and simple in design so as to require no extraordinary skill or knowledge to use such devices, and which removes moisture from the rebreathed air and which therefore minimizes the possibility of harm which may occur from breathing very moist air.

Further objects and advantages of the present invention will be obvious from the following detailed description and drawings, wherein:

FIG. 2 is a front elevational view of the respiratory exerciser and rebreathing device shown in FIG. 1;

FIG. 3 is a side elevational view of the device shown in FIGS. 1 and 2;

FIG. 4 is a top plan view of the device;

FIG. 5 is a horizontal cross sectional view of the respiratory exerciser device taken on line 5—5 of FIG. 2;

FIG. 6 is a vertical cross sectional view taken on line 6—6 of FIG. 2, revealing the adjustable slide and the exhalation valve of the device;

FIG. 7 is a vertical cross sectional view of the device taken on lne 7—7 of FIG. 2, revealing the moisture removing means and the inhalation valve of the device;

FIG. 8 is a horizontal cross sectional view of the device taken on line 8—8 of FIG. 3, the cross section revealing the relative positioning of the various chambers of the device in respect to one another;

FIG. 9 is a vertical cross sectional view taken on line 9—9 of FIG. 3, further showing the relationship of the various chambers of the device;

FIG. 10 is a vertical cross sectional view similar to that of FIG. 6, but showing only the adjustable slide, in a different position than that of FIG. 6; and FIG. 11 is another vertical cross sectional view similar to FIG. 10, but showing the slide in yet another position.

Figure 1:
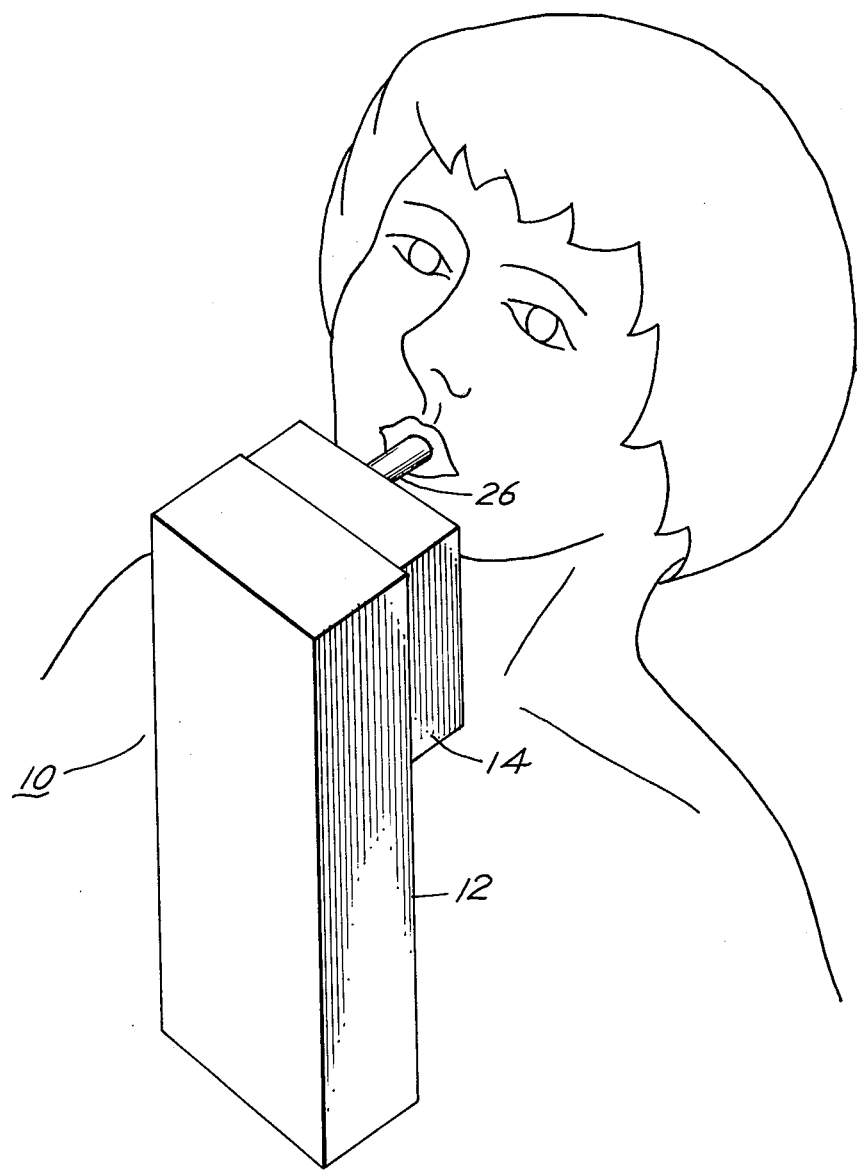
FIG. 1 is a perspective view of a person using the respiratory exerciser and rebreathing device of the present invention.

Referring more specifically to the drawings and to FIG. 1 in particular, numeral 10 indicates an adjustable respiratory exerciser and rebreathing device constructed in the manner of the present invention. The device consists generally of an air supply and mixing box 12 composed of four outer walls and a top, and a valve box 14 having three side walls, a top and a bottom, attached to the air supply box by screws 16, 18, 20 and 22. A gasket 24 is disposed between all adjacent surfaces of valve box 14 and air supply mixing box 12, thereby creating an air tight seal between them. Extending outwardly from the front of valve box 14 is mouthpiece stem 26, which may be fitted with any conventional mouthpiece or breathing mask apparatus, or may be used directly by placing one's lips around it as illustrated in FIG. 1. Interior walls 28 and 30 divide valve box 14 into essentially three sections, consisting of mouthpiece chamber 32, inhalation valve 34 and exhalation valve 36. Within inhalation valve 34, a partition 40 divides the valve into a lower chamber 42 and an upper chamber 44 and a hole 46 in partition 40 permits the passage of air between the lower and upper chambers. A valve element or ball 48 of a diameter somewhat larger than the diameter of hole 46 is disposed in upper chamber 44 and is constructed of light plastic material on cork. This ball, when seated in hole 46, prevents the passage of air between upper chamber 44 and lower chamber 42. An opening 50 connects lower chamber 42 and air supply mixing box 12 through which air may be drawn, and another opening 52 connects upper chamber 44 and mouthpiece chamber 32.

The construction of exhalation valve 36 is similar to that of inhalation valve 34. A partition 60 divides exhalation valve 36 into a lower chamber 62 and an upper chamber 64, and a hole 66 permits the passage of air between the chambers, and a ball 68 in upper chamber 64 seats over hole 66, thereby closing it and preventing the passage of air. In exhalation valve 36, however, an opening 70 connects lower chamber 62 and mouthpiece chamber 32, and a second opening 72 connects upper chamber 64 and air supply mixing box 12.

Air supply and mixing box 12 is divided by a wall 80 into essentially two portions, one being exhalation chamber 82 and the other inhalation chamber 84. Air box 12 is open on its bottom end; however, a floor portion 86 is positioned in inhalation chamber 84. A movable wall portion 88 is slidably mounted adjacent partition wall 80 in channels formed by side bumpers 90 and 92 and retention plates 94 and 96 held to wall 80 by a plurality of screws 98. Hole pairs 102, 104 and 106 are positioned in partition wall 80 to allow the passage of air between exhalation chamber 82 and inhalation chamber 84. Slidable wall 88 has hole pairs 112, 114 and 116 so placed that for various positions of slidable wall 88 only one pair of holes matches with holes in partition wall 80. Thus, in the uppermost position of the wall, hole pairs 102 and 112 match as shown in FIG. 6. When slidable wall 88 is partially withdrawn, hole pairs 104 and 114 match, and when slidable wall 88 is more fully withdrawn, hole pairs 106 and 116 match. The latter two positions of slidable wall 88 are clearly shown in FIGS. 10 and 11, respectively. For any position of slidable wall 88, only one pair of holes on slidable wall 88 will match with one pair of holes in partition wall 80, thereby allowing air to pass only through the one set of matched hole pairs.

Slidable wall 88 is retained in the pre-selected position by a retention device 120, consisting of an external knob 122 and a shaft 124 extending through partition 80. The inner end of shaft 124 has a hooked portion 126 which curves toward slidable wall 88. Three notches 132, 134 and 136 in slidable wall 88 will receive the end of hooked portion 126 when the wall is properly positioned. These notches are placed in wall 88 so that one of the notches will receive hooked portion 126 when the respective hole pairs of slidable wall 88 and partition 80 are aligned. The slidable wall is released by depressing knob 122, thereby removing hooked portion 126 from the notch. A compression spring 138 holds the hook in the notch when the knob is not depressed. A finger hole 140 is provided in slidable wall 88 to facilitate sliding of the wall.

Within inhalation chamber 84, condensation plates 150, 152, 154 and 156 are positioned between partition wall 80 and the outer wall of the air supply mixing box 12, and a top plate 158 closes the upper opening of the space between the condensation plates. Air entering inhalation chamber 84 through any of the aligned hole pairs must travel downward in the channels formed by the condensation plates, partition wall 80 and the outer wall of box 12, exit through the channels at the bottom of the condensation plates, and then travel upward in inhalation chamber 84 to reach and exit through hole 50. These plates provide increased surface area for the condensation of moisture from the air which is to be rebreathed. Cutouts such as shown at numerals 160 and 162 are provided in the portion of each condensation plate which crosses hole pairs 102, 104 and 106, to permit the air to flow freely through the holes. An opening 170 is disposed in floor portion 86 and has a downward extending tubular wall 172. A cap 174 is provided to close the opening of the downward extending wall 172 when the device is to be used.

In the use and operation of the present respiratory exerciser and rebreathing device constructed in the manner of the foregoing description, a breathing mask may be fitted on stem 26, or the user may place his mouth directly thereon, as seen in FIG. 1. If a nose and mouth mask is not used, the user of the device must be careful to breathe only through his mouth and into the device to achieve the full benefits. Beginning with the exhalation phase of respiration, the user exhales into the mouthpiece, thereby forcing air into mouthpiece chamber 32. The increased pressure within mouthpiece chamber 32 will force air through openings 52 and 70 into, respectively, the upper chamber 44 of inhalation valve 34 and the lower chamber 62 of exhalation valve 36. The increased air pressure in upper chamber 44 will merely force ball 48 tighter into the opening 46 of partition 40, thereby preventing passage of air between upper chamber 44 and lower chamber 42 of inhalation valve 34. However, the increased air pressure in lower chamber 62 of exhalation valve 36 will force the ball 68 off its seat over hole 66 in partition 60, and air then passes from lower chamber 62 to upper chamber 64.

Opening 72 permits the exhaled air to pass from upper chamber 64 into the exhalation chamber 82 of air supply and mixing box 12. The positive pressure entering chamber 82 forces the air within chamber 82 downward and normally out the open bottom of the chamber. Exhalation chamber 82 becomes substantially filled with only exhaled air.

During the inhalation phase, negative pressure is created in mouthpiece chamber 32 as the user inhales; therefore, air is drawn from lower chamber 62 of exhalation valve 36 and upper chamber 44 of inhalation valve 34 through holes 70 and 52, respectively. The decreased pressure or partial vacuum in lower chamber 62 causes ball 68 to seat more firmly onto opening 66 of partition 60 because of the higher relative pressure in upper chamber 64, thereby preventing passage of air between upper chamber 64 and lower chamber 62 of exhalation valve 36. The negative air pressure created in upper chamber 44, and the resultant relative positive pressure in lower chamber 42 of inhalation valve 34 cause ball 48 to unseat from opening 46. When ball 48 is displaced, air may pass between lower chamber 42 and upper chamber 44 of inhalation valve 34. As the relative negative pressure passes throughout the system, air passes from inhalation chamber 84 through hole 50, and throughout valve 34 into mouthpiece chamber 32 to be inhaled therefrom by the user of the device. The negative pressure in inhalation chamber 84 is compensated for by the passage of air from exhalation chamber 82 into inhalation chamber 84. As air is drawn out of exhalation chamber 82, it is replaced with air entering the bottom open portion of the device. Thus, a certain amount of mixing occurs within exhalation chamber 82 between exhaled air and room air entering the chamber. For any matched hole pair openings in partition 80 and slidable wall 88, the exhaled air in exhalation chamber 82 above the open hole pairs remains essentially stagnant during the inhalation phase and does not enter into the mixing process. Depending on the positioning of slidable wall 88 and the matching of hole pairs 102, 104 and 106 with hole pairs 112, 114 and 116, greater or lesser amounts of ambient air are drawn into inhalation chamber 84. Upper hole pairs 102 and 112 provide substantially less room air and more exhaled air than do hole pairs 106 and 116 of the lower portion of slidable wall 88 and partition wall 80. Thus, depending upon the positioning of slidable wall 88, the user of the respiratory exerciser and rebreathing device may rebreath more, or less, carbon dioxide.

The very warm and moist exhaled air which passes between exhalation chamber 82 and inhalation chamber 84 during the inhalation phase of the exercise flows along condensation plates 150, 152, 154 and 156. These somewhat cooler plates, when in contact with the warm moist air, cause a substantial amount of the moisture to precipitate out of the rebreathed air, forming tiny water droplets on the plates. This removes a substantial amount of the moisture from the air, thereby providing much drier air for the user of the device to rebreathe and thereby preventing complications which may occur when very moist air is breathed.

Normally a person with an underdeveloped respiratory system will move slidable wall 88 so that the lowest hole pairs 106 and 116 will align. This provides intake of the greatest amount of room air, therefore a lesser concentration of carbon dioxide and a higher concentration of oxygen. The dry room air drawn in also aids in the drying of the exhaled air. As the user progresses in the exercise and further develops his respiratory system, he may adjust slidable wall 88 by depressing knob 122 and moving the wall to align higher hole pairs and to rebreathe greater amounts of exhaled air and lesser amounts of ambient air, thereby inhaling greater amounts of carbox dioxide, which will create higher carbon dioxide levels in the blood and therefore develop the efficiency of the respiratory system. As further progress is made in the development of the respiratory system, the user may wish to rebreathe higher concentrations of carbon dioxide than permitted by adjustment of slidable wall 88. In that event, the user may partially restrict the opening at the bottom of the air supply and air mixture box, thereby allowing less air to enter the box and therefore less mixing of ambient air with carbon dioxide in chamber 82. This will provide a higher concentration of carbon dioxide for rebreathing, for any hole pair alignment.

In the embodiment shown in FIG. 1, balls 48 and 68 are made of cork. If one wishes to further exercise the muscles of respiration, the cork balls may be replaced with balls made of heavier material 40 that the user must exhale or inhale more forcefully to unseat the ball and open either valve. The increased force required will place a strain on the muscles of respiration, and thereby exercise these muscles, strengthening and developing them. Balls of differing weights can be used in each valve, and they can be interchanged as required to achieve the desired differential in level of inhalation and exhalation force. One may, for example, desire to have the inhalation ball be light and the exhalation ball relatively heavy.

Upon completion of an exercise period, knob 122 is depressed, and slidable wall 88 is completely removed from exhalation chamber 82 and cap 174 is removed, thereby opening hole 170. Air may then circulate through inhalation chamber 84, entering and exiting through holes 102, 104 and 106 as well as hole 170. The relatively dry room air passing through the inhalation chamber will dry the moisture which has collected within inhalation chamber 84. In a relatively short period of time, substantially all of the moisture within the entire respiratory exerciser and rebreathing device will have evaporated.

It can be seen that this device is very easily hand held and is simple in design and requires little or no special knowledge in its operation. The size and the proportions of the parts of the device can vary depending on its intended use. It can be used anywhere at virtually any time. In just a few moments a user of this device can perform a strenuous respiratory exercise without having to perform bodily physical exercise or engage in the physical strain which normally accompanies such a respiratory exercise as jogging, swimming, playing racquet ball, or the like. Thus, one who does not have the time to perform such physical exercises can accomplish the same respiratory exercise in a relatively short period of time through the use of this device. Also, those with physical infirmities, who cannot perform physical exercise, can maintain a well developed and efficiently functioning respiratory system through the use of this device.

In a modification of the aforedescribed embodiment, inhalation chamber 84 is filled with an air drying agent or material such as soda lime which will filter the air inhaled and further dry the air. In this modified form, hole 50 must be provided with a filter mechanism to prevent the passage of minute particles or dust from the desicant to the user. For this reason, the condensation plate design is preferred for home use over the device having the soda lime or other drying agent. It should additionally be noted that the hole pairs 102 and 112 positioned at the top of slidable wall 88 and partition wall 80, which provide the greatest amount of rebreathed air, also provide the greatest amount of moisture in the air. In the design of the preferred embodiment, this air passes along the greatest surface area of condensation plates and therefore has the greatest opportunity for condensation.

Although one embodiment and one modification have been disclosed in detail herein, various other changes can be made without departing from the scope of the present invention.

I claim:

1. A respiration exerciser and rebreathing device comprising walls forming first and second chambers, connection means therebetween for the passage of air, a mouthpiece for breathing into and out of said device, valve means including first and second passages connected to said first and second chambers, respectively, for regulating air flow between said mouthpiece and said first and second chambers so as to permit the passage of exhaled air from said mouthpiece into said first chamber and to supply inhaled air from said second chamber to said mouthpiece, and air flow means for connecting said first chamber to ambient air and for mixing outside air with exhaled air flowing through said first chamber and through said connection means thereby varying the carbon dioxide level in the air entering said second chamber.

2. A respiration exerciser and rebreathing device as defined in claim 1 in which said air flow means includes an opening at one end of said first chamber connecting said first chamber to atmosphere and said passage to said first chamber is connected to said first chamber in opposing relation to said opening and said connection means between said first and second chambers is disposed between said last mentioned passage and said opening, whereby the exhaled air mixes with ambient air before passing through said connection means to said second chamber.

3. A respiration exerciser and rebreathing device as defined in claim 2 in which said connection means between said first and second chambers includes a partition having a series of longitudinally spaced holes therein, and means to selectively open and close said holes.

4. A respiration exerciser and rebreathing device as defined in claim 3 in which said means to selectively open and close said series of holes is a slidable wall portion adjacent said partition and having holes registerable with said series of holes.

5. A respiration exerciser and rebreathing device as defined in claim 4 in which a plurality of condensation plates are disposed in said second chamber.

6. A respiration exerciser and rebreathing device as defined in claim 5 in which said valve means includes a mouthpiece chamber extending from said mouthpiece, first and second valves having upper and lower portions with openings therebetween, a valve element for closing each of said openings between said upper and lower portions, an opening between said lower portion of said first valve and said mouthpiece chamber, and an opening in said upper portion of said second valve and said mouthpiece chamber, said first passage being connected to the upper portion of said first valve and said first chamber, and said second passage being connected to the lower portion of said second valve and said second chamber.

7. A respiration exerciser and rebreathing device as defined in claim 6 in which said valve means has an adjustable element to require variable levels of inhalation and exhalation force to open said valve means and operate said device.

8. A respiration exerciser and rebreathing device as defined in claim 7 in which said adjustable element is a pair of spheres of differing weights which can be interchanged in said first and second valves to require varying forces of inhalation and exhalation to unseat said spheres and open said valves.

9. A respiration exerciser and rebreathing device as defined in claim 1 in which said connection means between said first and second chambers includes a partition having a series of longitudinally spaced holes therein, and means to selectively open and close said holes.

10. A respiration exerciser and rebreathing device as defined in claim 9 in which said means to selectively open and close said series of holes is a slidable wall portion adjacent said partition and having holes registerable with said series of holes.

11. A respiration exerciser and rebreathing device as defined in claim 10 in which a retractable pin extends through said partition, and said slidable wall contains notches in one edge thereof and a hooked portion on the end of said pin seats in said notches to secure said slidable wall portion in its pre-selected position.

12. A respiration exerciser and rebreathing device as defined in claim 1 means is disposed in said second chamber for removing moisture from said air passing therethrough.

13. A respiration exerciser and rebreathing device as defined in claim 7 in which said means for removing moisture includes a plurality of condensation plates.

14. A respiration exerciser and rebreathing device as defined in claim 1 in which said valve means includes a mouthpiece chamber extending from said mouthpiece, first and second valves in said first and second passageways, respectively, having upper and lower portions with openings therebetween a valve element for closing each of said openings between said upper and lower portions, an opening between said lower portion of said first valve and said mouthpiece chamber, and an opening in said upper portion of said second valve and said mouthpiece chamber, said first passage being connected to the upper portion of said first valve and said first chamber, and said second passage being connected to the lower portion of said second valve and said second chamber.

15. A respiration exerciser and rebreathing device as defined in claim 14 in which said valve means has an adjustable element to require variable levels of inhalation and exhalation force to open said valve means and operate said device.

16. A respiration exerciser and rebreathing device as defined in claim 15 in which said adjustable element is a pair of spheres of differing weights which can be interchanged in said first and second valves to require varying forces of inhalation and exhalation to unseat said spheres and open said valves.

* * * * *